United States Patent [19]

Kimura et al.

[11] 4,051,178

[45] Sept. 27, 1977

[54] PROCESS FOR PRODUCING TEREPHTHALIC ACID

[75] Inventors: Tsuneo Kimura; Hiroshi Hashizume; Yoshiaki Izumisawa, all of Kitakyushu, Japan

[73] Assignee: Mitsubishi Chemical Industries Limited, Tokyo, Japan

[21] Appl. No.: 694,361

[22] Filed: June 9, 1976

[30] Foreign Application Priority Data

June 25, 1975  Japan ................................. 50-79279

[51] Int. Cl.² ............................................. C07C 51/42
[52] U.S. Cl. ................................................. 260/524 R
[58] Field of Search ..................................... 260/524 R

[56] References Cited

U.S. PATENT DOCUMENTS 3,846,487  11/1974  Shigeyasu et al. .................... 260/524

FOREIGN PATENT DOCUMENTS 40-12695  6/1965  Japan .................................... 260/524

Primary Examiner—James O. Thomas, Jr.
Assistant Examiner—A. Siegel
Attorney, Agent, or Firm—Bierman & Bierman

[57] ABSTRACT

There is disclosed a process for producing terephthalic acid in which the reaction temperature range and the proportion of catalyst components of a cobalt compound, a manganese compound and at least one bromine compound are specifically chosen to produce a high grade terephthalic acid suitable for direct polycondensation in the production of polyester.

7 Claims, No Drawings

PROCESS FOR PRODUCING TEREPHTHALIC ACID

This invention relates to a process for producing terephthalic acid and, in more particular, to an improvement on a process for producing terephthalic acid having high purity and suitable for in preparing polyester by so-called direct esterification of direct polycondensation process, without the need for additional costly purification. Recently, the trend has been to prepare polyester such as polyethylene terephthalate from terephthalic acid, instead of dimethyl terephthalate which is converted into polyester through interesterification. It is essential that terephthalic acid suitable for direct polycondensation in preparing polyester be of excellent quality, for example, with an impurity content, in terms of 4-carboxybenzaldehyde, of less than 300 ppm. To achieve this standard, terephthalic acid produced by a known oxidation process should, in general, be subjected to a costly and complicated purification process.

In order to produce high purity terephthalic acid, various processes have already been proposed. For example, British Pat. No. 1241298 issued on 6 Oct., 1971 teaches that p-xylene is oxidized at a temperature of from 150° to 200° C in the presence of a Co-Mn-Br catalyst the main ingredient of which is cobalt in an atomic ratio of Mn to Co of less than 1. However, the product of this process is not suitable for direct polymerisation in polyester preparation because of the high 4-carboxybenzaldehyde content and the low transmittance value of an alkaline solution of the product, said value being indicative of the discoloration of the polyester derived therefrom. This is because of the relatively low reaction temperature which results in the formation of undesirable oxidation intermediates, such as 4-carboxybenzaldehyde, which are entrained in the crystals of the final product and are hardly removable.

Such defects will be avoided by using a large-sized reaction vessel and/or prolonging the reaction time, although to do so is economically disadvantageous and brings about increased loss of the solvent by burning out, that is, decomposition of the acetic acid solvent into carbon oxides.

Japanese Patent Publication No. 36732/1970 deals with a Co-Mn-Br catalyst system wherein the content of Mn is less than 20% by weight on the basis of Co.

With the use of this catalyst, however, high purity terephthalic acid is obtainable if only the catalyst is used in a relatively large amount of, for example, more than 3000 ppm for the solvent employed. Further, it is noted that, at a reaction temperature of from 170° to 200° C which is the range recommended by the inventors, the transmittance of an alkaline solution of the product is improved, but the content of 4-carboxybenzaldehyde and the burning of the solvent are found to be an unacceptable level. On the other hand, if an attempt is made to reduce the content of 4-carboxybenzaldehyde, then the productivity decreases remarkably. At a high reaction temperature, there are observed an increase in the content of 4-carboxybenzaldehyde, loss of the solvent by burning out and a decrease in the transmittance value.

The inventors have conducted intensive studies to find oxidation reaction conditions under which terephthalic acid is produced from p-xylene with high catalytic activity (i.e. requiring less catalyst), less burning of the solvent and high purity of the final product, and this invention has been accomplished from the knowledge that the abovementioned objects are achieved by appropriate selection of the proportion and composition of Co, Mn and Br in the catalyst system and selection of a temperature range within which p-xylene is oxidized in a liquid phase.

Therefore, according to this invention, there is provided a process for producing terephthalic acid which comprises oxidizing p-xylene in acetic acid with an oxygen-containing gas at a temperature of from 205° to 225° C in the presence of a catalyst consisting essentially of a cobalt compound in an amount, in terms of Co, of from 200 to 600 ppm for the solvent, a manganese compound in an amount, in terms of Mn, of from 0.5 to 1.5 times that of Co by weight and at least one bromine compound selected from the group consisting of hydrogen bromide, manganese bromide and cobalt bromide in an amount, in terms of Br, of from 400 to 2000 ppm for the acetic acid.

In carrying out the oxidation of p-xylene in a liquid phase with an oxygen-containing gas in the presence of a catalyst according to this invention, any known oxidation process, for example, as disclosed in U.S. Pat. No. 2,833,816 may basically be employed so far as the components and their proportion in the catalyst and the oxidation temperature range specified in this invention are satisfied. The oxidation according to this invention may conveniently be performed either in a continuous or semi-continuous process, but the former process is especially advantageous from technical points of view. Acetic acid which is the reaction solvent may contain a minor amount of water, for example, up to 30% by weight.

The catalyst with which the oxidation of p-xylene into terephthalic acid is promoted consists essentially of a cobalt compound, a manganese compound and at least one bromine compound.

Examples of the cobalt compound which may be employed according to this invention include, for example, cobalt acetate, cobalt naphthenate, cobalt carbonate and cobalt bromide. The amount to be used is, in terms of Co, in general, from 200 to 600 ppm, preferably 250 to 500 ppm and more preferably 300 to 400 ppm for the solvent.

Examples of the manganese compound which may be used in this invention include, for example, manganese acetate, manganese naphthenate, manganese carbonate and manganese bromide. The amount to be used is, in terms of Mn, from 0.5 to 1.5 times and preferably 0.7 to 1.3 times that of Co by weight. If the amount of the manganese compound departs from either the lower or the upper limit abovementioned, desired high purity terephthalic acid will never be obtained.

With respect to the bromine compound, it is essential to use at least one compound selected from the group consisting of hydrogen bromide, manganese bromide and cobalt bromide. Other bromine compounds such as sodium bromide, potassium bromide, ammonium bromide and tetrabromethane have low catalytic activity, and, therefore, the intended effect cannot be expected.

The amount of bromide compound to be used is, in terms of Br, from 400 to 2000 ppm and preferably 700 to 1500 ppm for the solvent and in such a proportion, in terms of Br, of more than 2.0 times and preferably more than 2.5 times that of Co by weight.

Too large an amount of bromine does not contribute to improve the quality of the resulting terephthalic acid; rather, it makes it necessary to recover the bromine compound for reuse. On the other hand, too small an amount results in the decrease in purity.

Cobalt bromide or manganese bromide acts as both the bromine compound and the cobalt or manganese compound in the catalyst.

According to this invention, we have found, it is essential to subject the p-xylene to a liquid phase oxidation in the presence of a catalyst having the abovementioned specific formulation at a temperature of from 205° to 225° C; if a reaction temperature outside the above range is used, little or no improvement can be expected even if our specific catalyst is used.

Heretofore, in the production of terephthalic acid suitable for direct polycondensation in the preparation of polyester, the oxidation of p-xylene was effected at a temperature of less than 200° C, because a temperature above 200° C has been found to result in a low grade terephthalic acid and the burning of a large amount of acetic acid. Therefore, it is believed that this invention achieves unexpected and surprising results in that the oxidation process of p-xylene is carried out at a temperature above 200° C to obtain terephthalic acid of high purity with less burning of acetic acid.

The pressure under which the oxidation according to this invention is carried out, not being critical so far as the reaction mass into which an oxygen-containing gas is introduced is maintained in a liquid state, ranges, in general, from 10 to 50 Kg/cm$^2$.

The oxygen-containing gas may be oxygen containing an inert gas in an amount of from 0 to 95%; in particular it is air. The total amount of oxygen to be supplied to the reaction system is in general 1 to 100 moles and preferably 3 to 100 moles per p-xylene to be oxidized. Where air is used, it is supplied at such a rate that the exhaust gas from the reaction vessel contains 1.5 to 8% and preferably 3 to 5% oxygen by volume.

The reaction product which is obtained in the form of slurry containing solid terephthalic acid is subjected to crystallization and a liquid-solid separation in conventional way. If desired, solid terephthalic acid thus obtained is washed with water or acetic acid. It is preferred to carry out such washing by suspending solid terephthalic acid in water or acetic acid and the resulting slurry is subjected again to a solid-liquid separation to obtain solid terephthalic acid.

This invention will be explained in detail by means of the following Examples. However, it should be understood that this invention is in no way limited by these Examples and various modifications may be made without departing from the spirit of this invention.

The various measurements and definitions referred to herein are given below.

Transmittance (T340)

The transmittance is measured with a solution of 7.5 g of terephthalic acid in 50 cc of 2N aqueous potassium hydroxide in a spectrophotometer (Model 101, available from Hetachi Ltd. Tokyo, Japan) using a cell having an internal size of 1 cm and a wave length of 340 m$\mu$.

Burning

The burning is calculated on the basis of the amounts of CO and $CO_2$ (which are decomposition products of acetic acid) in the exhaust gas from the reaction vessel in each run and the results are as expressed in Example 1 as being 1.

Total of catalyst

The total of catalyst is expressed in terms of the sum of Co, Mn and Br in cobalt, manganese and bromine compounds as ppm for the solvent.

EXAMPLE 1

A 10-liter capacity autoclave made of titanium and equipped with a reflux condenser, a stirrer, heating means, an inlet for p-xylene and oxygen-containing gas and an outlet for reaction product slurry was charged with:

| | | |
|---|---|---|
| Acetic acid | 2990 | g |
| Cobalt acetate tetrahydrate | 4.44 | g |
| Manganese acetate tetrahydrate | 4.68 | g |
| Hydrogen bromide (47% aq. soln.) | 6.70 | g |
| Water | 154 | g |

Under conditions of a temperature of 210° C, a pressure of 25 Kg/cm$^2$ and agitation of 500 rpm, p-xylene was supplied at a rate of 500 g/hr while air was introduced simultaneously at such a rate that the exhaust gas contained 4% oxygen by volume to effect oxidation for 2 hours. Then additional air was introduced for 1.5 minutes.

After being allowed to cool to 100° C, the reaction product in the form of slurry was recovered and subjected to separation, then the resulting terephthalic acid was mixed with 3 times that of acetic acid by weight and agitation was continued at 80° C for 20 minutes, followed by separating and drying the solid material.

The 4-carboxybenzaldehyde content and the transmittance of the product are given in Table 1.

EXAMPLES 2 – 10

For comparison purposes, procedures similar to those of Example 1 but with varying parameters as given in Table 1 were repeated.

The results are also given in Table 1.

Table 1

| Example No. | Catalyst | | | | | | Reaction Conditions | | | | |
|---|---|---|---|---|---|---|---|---|---|---|---|
| | Co (ppm) | Mn (ppm) | Br (ppm) | Mn/Co | Bromine Compd. | Total of Catalyst (ppm) | p-Xylene (g/hr) | Oxidation Temp. (° C) | $T_{340}$ | 4-CBA* (ppm) | Burning |
| 1 | 330 | 330 | 1000 | 1.0 | HBr | 1660 | 500 | 210 | 94.0 | 150 | 1.0 |
| 2 | 330 | 330 | 1000 | 1.0 | HBr | 1660 | 500 | 195 | 90.0 | 250 | 0.9 |
| 3 | 330 | 300 | 1000 | 0.91 | HBr | 1630 | 500 | 190 | 90.0 | 550 | 0.5 |
| 4 | 330 | 330 | 1000 | 1.0 | HBr | 1660 | 500 | 230 | 88.0 | 332 | 1.9 |
| 5 | 330 | 250 | 1000 | 0.758 | HBr | 1580 | 500 | 230 | 86.0 | 352 | 1.8 |
| 6 | 330 | 600 | 1000 | 1.82 | HBr | 1830 | 500 | 210 | 83.0 | 170 | 1 |
| 7 | 330 | 150 | 1000 | 0.455 | HBr | 1480 | 500 | 210 | 90.0 | 250 | 0.9 |
| 8 | 1000 | 100 | 3000 | 0.1 | HBr | 4100 | 500 | 190 | 93.7 | 280 | 0.7 |
| 9 | 1000 | 100 | 3000 | 0.1 | HBr | 4100 | 250 | 190 | 94.0 | 200 | 1.4 |
| 10 | 1000 | 100 | 3000 | 0.1 | HBr | 4100 | 500 | 210 | 92.0 | 250 | 1.4 |

Note:
*4-Carboxybenzaldehyde.

From the above results, the following conclusions are derived.

Examples 2 and 3 show that a low reaction temperature results in terephthalic acid containing a large proportion of impurities as indicated by the low transmittance.

In Examples 4 and 5, higher reaction temperature is employed; then the content of impurities does not decrease to substantial extent in consequence the product has low transmittance and the burning of the solvent increases.

From Examples 6 and 7, it is clear that the use of a manganese compound and a cobalt compound in a proportion higher or lower than in the specified range results in the formation of an inferior product. In Example 8, with a catalyst containing a low proportion of a manganese compound, a low reaction temperature (i.e. 190° C) is employed and the burning of the solvent is reduced, but the final product contains a high proportion of impurities.

In Example 9 which is similar to Example 8 excepting that the feeding rate of p-xylene is reduced, the quality of terephthalic acid is improved, but the productivity is decreased with a large amount of acetic acid being lost by burning.

In Example 10, with a catalyst containing a low proportion of a manganese compound, a reaction temperature of 210° C produces a lower grade final product and increases the amount of acetic acid burnt.

Moreover, Examples 8 to 10 require a far larger total of catalyst.

EXAMPLES 11 to 16

(Semicontinuous Process)

An apparatus as in Example 1 was employed and the various catalysts and reaction conditions listed in Table 2 were employed to oxidize p-xylene to terephthalic acid.

The results are also given in Table 2.

tic acid by burning even at a relatively high reaction temperature.

EXAMPLES 17 and 18

(Continuous process)

The reaction vessel employed was similar to that of Example 1 excepting that an outlet for the reaction product slurry at a height of 45% of the reactor height from the bottom and an inlet for the solvent were provided.

Raw materials in the amounts given in Example 1 were charged in the vessel and the procedures in Example 1 were repeated to effect oxidation for two hours; then p-xylene and aqueous acetic acid containing the catalyst components and water in the proportion given in Example 1 were charged at a rate of 400 g/hr and 1200 g/hr, respectively, and, at an interval of 30 minutes, the reaction product was discharged until the level of the reaction mass reached the position of the outlet for the product. After 12 hours from the start of the reaction, the supply of p-xylene was stopped. The air was blown into the discharged slurry for 1.5 minutes. The slurry was subjected to washing treatment according to the procedures of Example 1.

For comparison, the oxidation reaction was repeated according to the reaction conditions of Example 8.

The reaction conditions and results of Examples 17 and 18 are given in Table 3.

Table 3

| | Catalyst | | | | | | Reaction Conditions | | | | |
|---|---|---|---|---|---|---|---|---|---|---|---|
| Example No. | Co (ppm) | Mn (ppm) | Br (ppm) | Mn/Co | Bromine Compd. | Total Catalyst (ppm) | p-Xylene (g/hr) | Oxidation Temp. (° C) | $T_{340}$ | 4-CBA* (ppm) | Burning |
| 17 | 330 | 330 | 1000 | 1.0 | HBr | 1660 | 400 | 210 | 92.0 | 190 | 0.8 |
| 18 | 1000 | 100 | 3000 | 0.1 | HBr | 4100 | 400 | 190 | 87.0 | 400 | 0.6 |

Note:
*4-Carboxybenzaldehyde.

We claim:
1. In a process for the production of terephthalic acid comprising oxidizing p-xylene in an acetic acid solvent with an oxygen-containing gas in the presence of a catalyst, the improvement which comprises the reaction temperature being from 205° C to 225° C, and said catalyst consisting essentially of
   a. a cobalt compound containing 200 to 600 parts of cobalt per million parts of said solvent,
   b. a manganese compound containing 0.5 to 1.5 times the weight of said cobalt of manganese, and

Table 2

| | Catalyst | | | | | | Reaction Conditions | | | | |
|---|---|---|---|---|---|---|---|---|---|---|---|
| Example No. | Co (ppm) | Mn (ppm) | Br (ppm) | Mn/Co | Bromine Compd. | Total of Catalyst (ppm) | p-Xylene (g/hr) | Oxidation Temp. (° C) | $T_{340}$ | 4-CBA* (ppm) | Burning |
| 11 | 330 | 330 | 1000 | 1.0 | HBr | 1660 | 950 | 220 | 94.0 | 170 | 1 |
| 12 | 330 | 250 | 1000 | 0.756 | HBr | 1580 | 500 | 210 | 93.5 | 160 | 0.9 |
| 13 | 330 | 330 | 1500 | 1.0 | HBr | 2160 | 500 | 210 | 94.0 | 160 | 1 |
| 14 | 330 | 330 | 900 | 1.0 | $CoBr_2$ | 1560 | 500 | 210 | 93.4 | 170 | 1 |
| 15 | 330 | 420 | 1000 | 1.27 | HBr | 1750 | 500 | 210 | 93.5 | 160 | 1 |
| 16 | 330 | 330 | 960 | 1.0 | $MnBr_2$ | 1620 | 500 | 210 | 93.2 | 170 | 1 |

Notes:
*4-Carboxybenzaldehyde

From the above results, it is clear that the process according to this invention gives many advantages, that is, with the use of a relatively small amount of catalyst, it makes possible high productivity, the production of high grade terephthalic acid and decreased loss of acec. a bromine compound taken from the class consisting of hydrogen bromide, manganese bromide, and cobalt bromide, said bromine compound comprising 400 to 2000 parts of bromine per million parts of said solvent.

2. A process for producing terephthalic acid according to claim 1, wherein said cobalt compound is cobalt acetate, said manganese compound is manganese acetate and said bromine compound is hydrogen bromide.

3. A process for producing terephthalic acid according to claim 1, wherein said catalyst consists essentially of cobalt bromide and manganese acetate.

4. A process for producing terephthalic acid according to claim 1, wherein said catalyst consists essentially of manganese bromide and cobalt acetate.

5. A process for producing terephthalic acid according to claim 1, wherein oxidation reaction product containing solid terephthalic acid is subjected to crystalization and solid-liquid separation, and the solid terephthalic acid thus obtained is washed with water or acetic acid.

6. A process for producing terephthalic acid according to claim 5, wherein said washing is carried out by suspending the solid terephthalic acid in water or acetic acid and the resulting slurry is subjected again to solid-liquid separation to obtain solid terephthalic acid.

7. A process for producing terephthalic acid according to claim 1, wherein said liquid phase oxidation step is continuously carried out.

* * * * *